(12) United States Patent
Sidhu et al.

(10) Patent No.: US 10,261,037 B2
(45) Date of Patent: Apr. 16, 2019

(54) MONITORING A STRUCTURE FOR DAMAGE

(71) Applicant: BAE SYSTEMSPLC, London (GB)

(72) Inventors: Jagjit Sidhu, Bristol (GB); Amir Rezai, Bristol (GB); David Andrew Cocksedge, Chelmsford (GB)

(73) Assignee: BAE Systems plc, London (GB)

( * ) Notice: Subject to any disclaimer, the term of this patent is extended or adjusted under 35 U.S.C. 154(b) by 28 days.

(21) Appl. No.: 15/536,760

(22) PCT Filed: Feb. 2, 2015

(86) PCT No.: PCT/GB2015/050260
§ 371 (c)(1),
(2) Date: Jun. 16, 2017

(87) PCT Pub. No.: WO2016/102909
PCT Pub. Date: Jun. 30, 2016

(65) Prior Publication Data
US 2017/0363557 A1   Dec. 21, 2017

(30) Foreign Application Priority Data

Dec. 23, 2014 (GB) .................................. 1423079.1

(51) Int. Cl.
| G01L 1/00 | (2006.01) |
| G01N 27/20 | (2006.01) |
| G01M 5/00 | (2006.01) |
| G01L 1/20 | (2006.01) |

(52) U.S. Cl.
CPC .......... G01N 27/20 (2013.01); G01M 5/0033 (2013.01); G01M 5/0083 (2013.01); *G01L 1/20* (2013.01)

(58) Field of Classification Search
CPC .. G01N 27/20; G01M 5/0033; G01M 5/0083; G01L 1/20
(Continued)

(56) References Cited

U.S. PATENT DOCUMENTS 3,803,485 A * 4/1974 Crites .................. G01N 27/205
                                                          324/693
4,603,252 A * 7/1986 Malek ..................... B29C 37/00
                                                          250/227.14
(Continued)

FOREIGN PATENT DOCUMENTS

| DE | 3426268 A1 | 1/1986 |
| EP | 2431412 A1 | 3/2012 |
(Continued)

OTHER PUBLICATIONS

Search Report under Section 17(5) of Application No. GB1423079.1, dated Apr. 30, 2015, 4 pages.
(Continued)

*Primary Examiner* — Max H Noori
(74) *Attorney, Agent, or Firm* — Maine Cernota & Rardin

(57) ABSTRACT

A structure to be monitored for damage and a method of monitoring the structure for damage are provided. The structure has a coating thereon, the coating defining a surface having characteristics which vary in a predetermined manner with damage to the structure. The surface has a series of conductive tracks applied thereto and in intimate contact therewith such that the said predetermined variation of the surface characteristics will vary the resistance of the series of conductive tracks in a predetermined manner in order to determine both location and extent of damage.

21 Claims, 2 Drawing Sheets

(58) Field of Classification Search
USPC .................................................. 73/763, 768
See application file for complete search history.

(56) References Cited

U.S. PATENT DOCUMENTS

| | | |
|---|---|---|
| 5,952,836 A | 9/1999 | Haake |
| 2005/0284232 A1 | 12/2005 | Rice |
| 2009/0294022 A1* | 12/2009 | Hayes .................. G01N 27/041 156/94 |
| 2010/0052704 A1 | 3/2010 | Fay et al. |
| 2010/0225497 A1 | 9/2010 | Marincak |
| 2011/0089958 A1 | 4/2011 | Malecki et al. |
| 2012/0197482 A1* | 8/2012 | Moser .................. G01M 5/0033 701/32.2 |
| 2012/0318925 A1* | 12/2012 | Gibson .................... B64G 1/52 244/158.3 |

FOREIGN PATENT DOCUMENTS

| | | |
|---|---|---|
| WO | 2007085070 A1 | 8/2007 |
| WO | 2008144023 A1 | 11/2008 |
| WO | 2012048237 A2 | 4/2012 |

OTHER PUBLICATIONS

International Preliminary Report on Patentability of International Application No. PCT/GB2015/050260, dated Mar. 22, 2017, 14 pages.
International Search Report and Written Opinion of International Application No. PCT/GB2015/050260, dated Aug. 25, 2015, 18 pages.

* cited by examiner

MONITORING A STRUCTURE FOR DAMAGE

RELATED APPLICATIONS

This application is a National Phase application filed under 35 USC § 371 of PCT Application No. PCT/GB2015/050260 with an International filing date of Feb. 2, 2015, which claims priority of GB Patent Application GB1423079.1 filed Dec. 23, 2014. Each of these applications is herein incorporated by reference in its entirety for all purposes.

FIELD OF THE INVENTION

The present invention relates to monitoring a structure for damage and to such a structure to be monitored.

BACKGROUND

The invention is applicable to any structure to be monitored although it is particularly applicable to structures of fibre reinforced plastics composite material where impact damage, in particular, can cause a degree of damage to the structure which is difficult to detect from a visual inspection of the impact surface. Such damage is known as "barely visible impact damage" or BVID. Thus what can appear, at the impact surface, as a small chip or crack, for example, may spread out under the surface into severe damage which may compromise the structure sufficiently to cause random failure or failure under only moderate loading.

In the context of structures which are structurally critical and where impact damage is likely, such as aircraft components like wing skins, protective helmets or body armour, such potential failure under normal loading or repeat impact is unacceptable. Currently, in order to protect against such risk, regular potentially expensive inspection must be carried out. Such inspection can be extremely time-consuming, can require expensive equipment and can mean that the structure, while out of service in the case of an aircraft for example, will be costing the operator money. In the case of helmets or body armour, small impacts may go unnoticed and the article may be presumed safe and undamaged whereas a further impact may cause catastrophic damage and endanger the user's life. Such helmets may be made of glass, carbon, Kevlar or other fibre reinforced plastics composite. Body armour may be made of ceramic material or, from carbon or Kevlar composite, and airframe components may typically be made of carbon fibre composite.

US 2005/284232 A1 discloses a structure to be monitored for damage by the application of a series of conductive tracks to a surface of the structure.

The principal aim of the invention is to efficiently detect damage to a helmet, body armour or other structure which is likely to be made of fibre reinforced plastics composite material and where damage may arise from impact or excessive loading.

SUMMARY

According to a first aspect of the invention there is provided a structure to be monitored for damage, the structure having a coating thereon, the coating defining a surface having specific failure characteristics tailored to the structure which vary in a predetermined manner with damage to the structure, the surface having a series of conductive tracks applied thereto and in intimate contact therewith such that the said predetermined variation of the surface characteristics will vary the resistance of the series of conductive tracks in a predetermined manner.

Using the example of a protective helmet, the internal surface of the helmet may be lined with a coating, for example a glassy polymer, a thermoset polymer, a cementitious ceramic or a mixture of polymers and fillers such that the coating has specific failure characteristics tailored to the structure. For example it may develop cracks or in extreme cases delaminate and flake when it undergoes an impact of a particular characteristic, or undergoes compressive or tensile loading above a specific value.

Alternatively, or in addition, the coating may develop cracks if repeatedly loaded with a loading which is sub-threshold for failure of the structure.

The coating characteristics may be controlled through choice of coating material, thickness of coating, curing characteristics of the coating or post curing treatments, for example.

The failure characteristics of the coating may be further controlled by loading the coating with stress concentrators such as crack initiators. These may be in the form of particulates, voids, tailored self-releasing surfaces or secondary induced micro-cracking, all dispersed throughout the coating.

The coating may be calibrated against the required loadings or damage state or states of the structure.

Damage may be detected using an array of directly written resistive or conductive tracks: a development of a crack will lead to a variation in the array paths associated with the cracked region.

The use of the Direct Write technique allows the printed tracks to have intimate contact with the coating and the tracks will be conformal to the shape of the structure/helmet.

The tracks may be printed using any of the known Direct Write techniques, such as ink jet, extrusion nozzle or micro spray printing.

The inks may be off-the-shelf resistive or conducting inks, although these may be mixed or modified to provide a specific resistance, as required.

The tracks may be written onto the coating in the form of interconnected arrays, such as grids, extending across the surface of the structure. The coating will normally be written onto a surface opposite to the surface subject to impacts. Thus, for a helmet, this will desirably be the inside surface of the helmet; for body armour it is likely to be the surface closest to the user's body, and for airframes it will desirably be the non-aerodynamic surface of any aerodynamic component such as a wing or fuselage skin, for example.

The sensitivity of resolution of the occurrence of damage may be adjusted by adjusting the track width and/or track separation.

A track array of between 50 and 100 tracks, in each of two orthogonal directions, may be suitable for a helmet, according to the invention.

A sensitivity of resolution of approximately 2 mm may be suitable for a helmet, according to the invention.

According to a second aspect of the invention there is provided a method of testing a structure for damage, the method including the steps of providing the structure with a coating defining a surface and having a series of conductive tracks applied to the surface in intimate contact therewith, the surface having specific failure characteristics tailored to the structure which vary in a predetermined manner with damage to the structure and the resistance of the series of conductive tracks being made variable in known relationship with the variation in surface characteristics of the surface, including measuring an electrical parameter of the series of tracks and comparing the measured parameter with the same parameter of the tracks when measured for the undamaged structure.

The parameter measured may be electrical resistance, voltage or current.

In addition, the method of interrogating the track array may allow greater resolution than would otherwise be possible for a given track width or track separation.

The series of conductive tracks may comprise a grid array having a series of electrical connections positioned around a periphery of the grid array and the method may include the step of operating monitoring means connected via said connections to the grid array to interrogate different combinations of connections whereby to determine a said electrical parameter for each combination followed by analysis of said parameters to determine a location on the structure of any said damage.

Determination of the location on the structure of any damage by analysis of the parameters may include making reference to results of previous calibration data for the structure.

The tracks may be interrogated using a multiplexing system. This may allow real time monitoring and localisation information to be obtained for any detected structural faults.

The structure may be monitored for damage remotely and the monitoring means may be connected to the structure directly, or wirelessly using transmission and receiving means.

BRIEF DESCRIPTION OF THE FIGURES

The invention may be performed in various ways, and, by way of example, an embodiment thereof will now be described, with reference to the accompanying drawings in which:—

DETAILED DESCRIPTION

Figure 1:
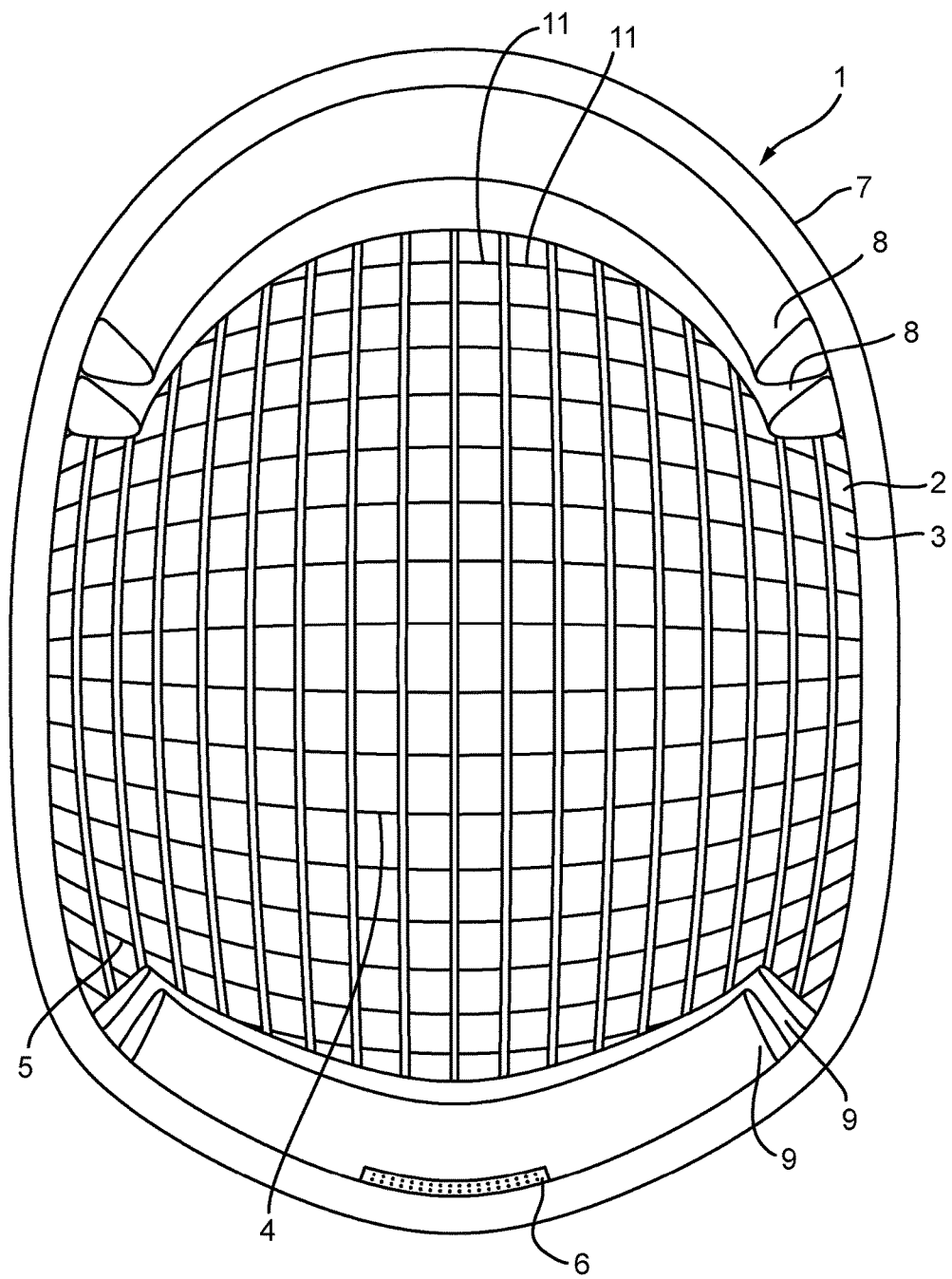
FIG. 1 shows, schematically, the interior of a protective helmet with conducting tracks printed onto an interior surface thereof.

Referring to the drawings, FIG. 1 shows a protective helmet 1 having an interior surface 2. The helmet 1 includes a protective shell 7 having front padding 8, rear padding 9 and internal padding and chin strap (removed and not shown, for clarity). The interior surface 2 is defined on an interior coating 3 for the helmet. The coating 3 is a glassy polymer which has been formulated to crack in response to impacts of a certain predefined type and amplitude occurring to the helmet 1. To calibrate the coating 3 in this way, coatings of various formulations were applied to the interior of the helmet. For each formulation of coating 3, the helmet was subject to impacts typically expected to occur to that type of helmet. Thus, for a military helmet, the helmet may be subject to various accidental knocks, both when worn and when not being worn. The helmet could also be dropped onto a hard surface. In battle, the helmet may be subject to various types of glancing blow, perhaps from a rifle butt or some other hard object. The helmet may even be struck a glancing blow from a projectile, such as a bullet or shrapnel.

Impacts designed to replicate such impacts were applied to the helmet and the visual effects on the coating noted.

In addition to a close inspection of the coating itself, a grid pattern 4 of conductive ink tracks 5 was printed onto the interior surface 2 of the coating 3, using direct write technology. Shown are eighteen ladder patterns 11 of the grid 4. The number of ladder patterns 11 may be increased or decreased according to the degree of damage resolution required. Terminals 6 are connectable to monitoring means 10 (see FIG. 3) capable of systematically applying test voltages to different pairs of terminals. Here, the monitoring means are directly connectable to the terminals 6. However, in practice, the terminals 6 may be connected to a transmitter 13 to transmit the state of the grid to remote monitoring means 12 which may be in the form of a hand-held terminal. Such an arrangement may be used for real time monitoring of the state of the helmet or structure.

Different types of impact to the helmet will cause differing extents and types of cracking in the coating 3. Each crack will cause a full or partial discontinuity in a printed track, thus affecting the overall conductivity of that track.

The monitoring means includes a computer to analyse the results of the applied voltages. The analysis of the results can be used to locate track discontinuities and therefore damage to the helmet 1. In fact, with a sufficiently sensitive grid 4 and monitoring means, it is possible to determine the shape and size of helmet damage.

The computer may be used to store results of helmet impacts, both test impacts and in-service impacts. The store can be interrogated whenever convenient, in order to determine the structural state of the helmet. Thus, for example, a helmet may be tested regularly for damage, according to the invention. A particular advantage of the invention is its ability to determine whether a particular impact, which may have seemed or been relatively light in nature, has inflicted unacceptable damage to a helmet or not. Fibre reinforced composite materials are notorious for suffering impact damage which can be serious but which is not easily seen at the surface. Ongoing monitoring of the structure/helmet may be used to monitor damage which has already occurred, to determine whether the damage has increased or stayed static, over time.

Figure 2:
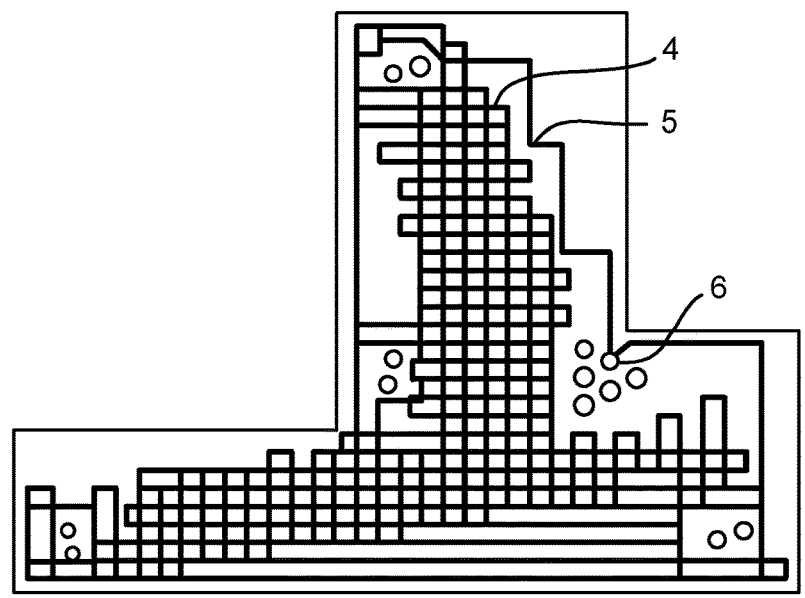
FIG. 2 shows a sample of printed tracks in the form of a grid.

FIG. 2 shows a sample directly written grid of the same type as could be used according to the invention. The grid pattern 4 of conducting tracks 5 extends over an area to be monitored. Interrogation of terminals 6 by monitoring means 10 can provide data for analysis in the same manner as for the grid of FIG. 1.

Figure 3:
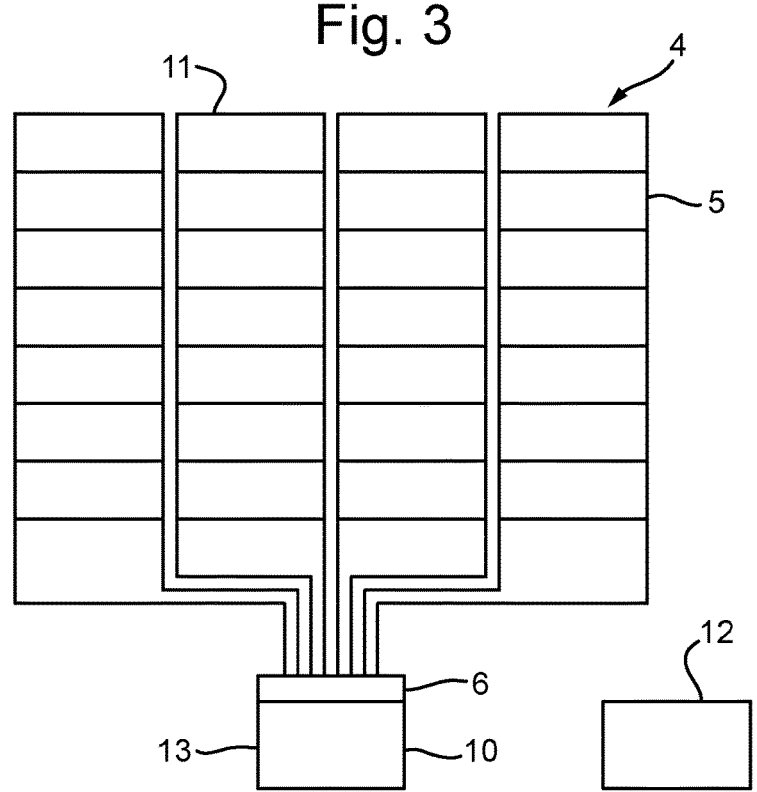
FIG. 3 shows a further sample grid using a ladder type structure.

FIG. 3 shows a simplified ladder type grid arrangement having a series of four ladders 11. This arrangement affords location of damage in longitudinal and lateral directions.

What is claimed is:

1. A structure to be monitored for damage, the structure having a coating thereon, the coating defining a surface having specific failure characteristics tailored to the structure which vary in a predetermined manner with damage to the structure, the surface having a series of conductive tracks applied thereto and in intimate contact therewith such that the said predetermined variation of the surface characteristics will vary the resistance of the series of conductive tracks in a predetermined manner, wherein the coating comprises crack initiators.

2. The structure according to claim 1, in which the variation in surface characteristics comprises cracking of the surface to an extent dependent upon the degree and/or type of damage to the structure.

3. The structure according to claim 1, in which the coating is a glassy polymer.

4. The structure according to claim 1, in which the coating is a thermoset polymer.

5. The structure according to claim 1, in which the coating is a mixture of polymers and fillers.

6. The structure according to claim 1, in which the coating is a cementitious ceramic.

7. The structure according to claim 1, in which the characteristics of the surface of the coating vary with damage to the structure which includes impact damage, damage due to compressive or tensile loading above a certain threshold or damage due to repeated loading below the said threshold.

8. The structure according to claim 1, in which a said conductive track is formed on the surface of the coating by a direct write process.

9. The structure according to claim 1, comprising a protective helmet in which the coating is applied to an interior surface of the helmet.

10. The structure according to claim 1, comprising an aircraft structural component.

11. The structure according to claim 1, in which the crack initiation means comprises particulates in the coating.

12. The structure according to claim 1, in which the crack initiation means comprises voids in the coating.

13. The structure according to claim 1, in which the crack initiation means comprises micro-cracking in the coating.

14. The structure according to claim 1, in which the coating is calibrated whereby to display the said variation in characteristics in response to a defined state of damage.

15. The structure according to claim 1, in which the series of conductive tracks comprises a grid array disposed across the structure.

16. The structure according to claim 15, including a series of electrical connections positioned around a periphery of the grid array and monitoring means connected via said connections to the grid array, the monitoring means being adapted to interrogate the grid array whereby to determine a location on the structure of any said damage.

17. The structure according to claim 16, in which the monitoring means is arranged to interrogate the grid array during use of the structure.

18. A method of testing a structure for damage, the method including the steps of providing the structure with a coating defining a surface and having a series of conductive tracks applied to the surface in intimate contact therewith, the surface having specific failure characteristics tailored to the structure which vary in a predetermined manner with damage to the structure and the resistance of the series of conductive tracks being made variable in known relationship with the variation in surface characteristics of the surface, including measuring an electrical parameter of the series of tracks and comparing the measured parameter with the same parameter of the tracks when measured for the undamaged structure, wherein the coating comprises crack initiators.

19. The method according to claim 18 in which the parameter measured is resistance.

20. The method according to claim 18, in which the series of conductive tracks comprises a grid array having a series of electrical connections positioned around a periphery of the grid array and the method includes the step of operating monitoring means connected via said connections to the grid array to interrogate different combinations of connections whereby to determine a said electrical parameter for each combination followed by analysis of said parameters to determine a location on the structure of any said damage.

21. The method according to claim 20, in which determination of the location on the structure of any damage by analysis of the parameters includes making reference to results of previous calibration data for the structure.

* * * * *